United States Patent [19]

Fogarty

[11] Patent Number: 4,608,984
[45] Date of Patent: Sep. 2, 1986

[54] SELF-RETRACTING DILATATION CATHETER

[76] Inventor: Thomas J. Fogarty, 770 Welch Rd., Palo Alto, Calif. 94304

[21] Appl. No.: 366,932

[22] Filed: Apr. 9, 1982

Related U.S. Application Data

[63] Continuation of Ser. No. 198,343, Oct. 17, 1980, abandoned.

[51] Int. Cl.⁴ ............................................. A61M 29/02
[52] U.S. Cl. .................................. 128/344; 128/348.1
[58] Field of Search ............ 128/344, 349 B, 349 BV, 128/325, DIG. 9, 348.1

[56] References Cited

U.S. PATENT DOCUMENTS

| | | | |
|---|---|---|---|
| 2,616,429 | 11/1952 | Merenlender | 128/350 |
| 2,688,329 | 9/1954 | Wallace | 128/349 |
| 3,426,744 | 2/1969 | Ball | 128/1 |
| 3,799,172 | 3/1974 | Szpur | 128/349 R |
| 3,837,347 | 9/1974 | Tower | 128/404 |
| 3,996,938 | 12/1976 | Clark | 128/348 |
| 4,046,151 | 9/1977 | Rose | 128/404 |
| 4,105,022 | 8/1978 | Antoshkiw et al. | 128/349 B X |
| 4,261,339 | 4/1981 | Hanson et al. | 128/348 X |

FOREIGN PATENT DOCUMENTS 512456  9/1939  United Kingdom ................ 128/344

Primary Examiner—Michael H. Thaler
Attorney, Agent, or Firm—Limbach, Limbach & Sutton

[57] ABSTRACT

A catheter is provided with a self-retracting inflatable section by forming the section of an inner non-elastic balloon and an outer elastic balloon, the latter being effective to collapse the former when the former is deflated. Further lateral retraction of the inflatable section is effected by axial twisting.

2 Claims, 4 Drawing Figures

U.S. Patent  Sep. 2, 1986  4,608,984
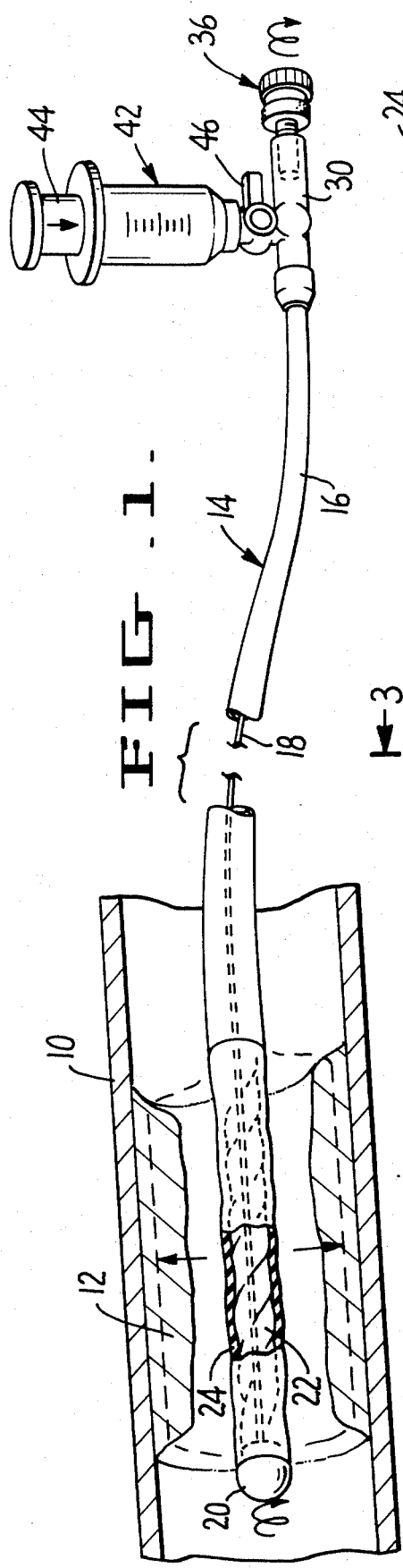
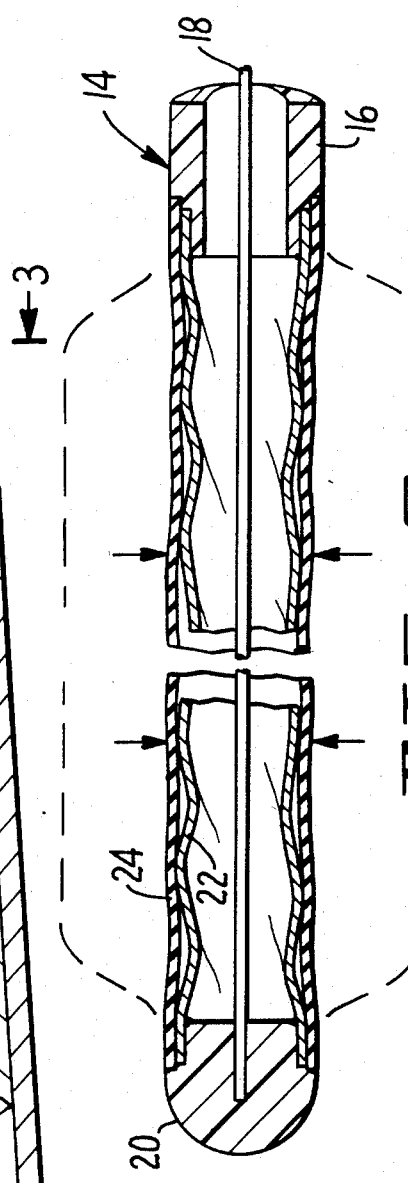
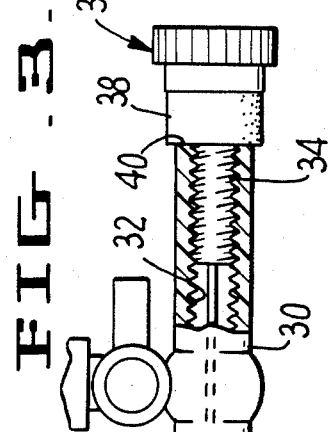
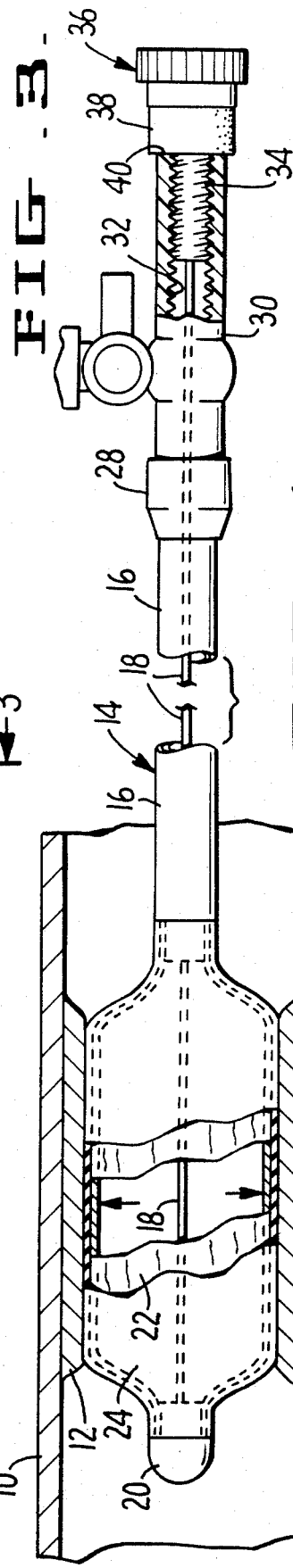

SELF-RETRACTING DILATATION CATHETER

This application is a continuation, of application Ser. No. 198,343, field Oct. 17, 1980, now abandoned.

RELATED APPLICATION

The subject catheter is an improvement upon the dilatation catheter disclosed in my co-pending application, Ser. No. 116,816, filed Jan. 30, 1980, now U.S. Pat. No. 4,292,974, for DILATATION CATHETER APPARATUS AND METHOD.

BACKGROUND OF THE INVENTION

The present invention relates to apparatus for use in dilating occluded blood vessels, and more particularly to an apparatus of that type wherein dilatation is achieved by means of a balloon element of large diameter which is inflated to compress the occlusion being treated and wherein the transverse dimension of the balloon element in non-inflated condition is sufficiently reduced to enable placement of the catheter properly within the lumen of an occluded artery or vein.

SUMMARY OF THE INVENTION

The essential purpose and object of the subject invention is to improve the catheter of my above-identified co-pending application so that the catheter would be self-retracting, i.e. so that the balloon element would automatically collapse when the inflation pressure was released. This is accomplished by providing another balloon element in enveloping relation to the first one, forming the additional balloon of an elastic material, and preconditioning the added balloon so that upon deflation of the inner balloon and consequent deflation of the outer one both balloons will have a combined lateral dimension which is less than the normal transverse dimension of the catheter. The transverse dimension of the two deflated balloons may then be further reduced somewhat by axially twisting the inner one.

DESCRIPTION OF THE DRAWING

FIG. 1 is a view in perspective of the catheter emplaced in an occluded artery.

FIG. 2 is an enlarged view in longitudinal section of the balloonable end of the catheter.

FIG. 3 is a view taken along lines 3—3 of FIG. 2.

FIG. 4 is a view partly in section and partly in elevation of the catheter in full dilated condition within the occluded artery.

DESCRIPTION OF THE PREFERRED EMBODIMENT

FIG. 1 illustrates a blood vessel 10 which is partially occluded by an extended occlusion 12. As shown, the vessel takes the form of an artery and the occlusion is what is commonly known as an arteriosclerotic plaque or atheroma. This is the type of adhering occlusion with which the subject apparatus is expected to find primary application. It should be understood, however, that the invention is applicable in treating other types of occluded vessels where dilatation is desired. For example, the catheter of the invention may be used in treating occlusions resulting from fibromuscular displasia in veins.

The catheter 14 comprises a flexible plastic tube 16, a guide wire 18 extending therethrough and fixedly attached to rounded tip member 20, an inner inflatable balloon element or bag 22 having its ends bonded to tube 16 and tip member 20, and an outer balloon element or bag 24 having its ends bonded to the end of balloon element 22 and being thereby secured to tube 16 and tip member 20. Tube 16 is fixedly attached to an internally threaded coupling member 28 which is attached to the externally threaded end of a T-shaped fitting 30. The proximal end of fitting 30 is provided with internal threads 32 with which the externally threaded stem portion 34 of control knob 36 is threadably engageable. The control knob 36 is attached to wire 18 so that rotation of the knob results in axial rotation of the wire. The control knob stem 34 is normally fully threadably engaged with fitting 30 to thereby position the sealing disc 38 carried by knob 36 in sealing engagement with the proximal end 40 of fitting 30.

A syringe 42 is connected to the proximal end of the catheter 14 through the fitting 30. The syringe is to be filled with an incompressible fluid. Syringe plunger 44 and control valve 46 constitute means whereby the fluid may be selectively charged into or released from balloon element 22 through the tube 16.

The catheter is used in the following manner. The knob 36 is rotated to back it off from the fitting 30 to approximately the position shown in FIG. 1. The wire 18 and tip 20 are thereby rotated to wind up or twist the balloon element 22 to reduce its non-inflated diameter to a value which is materially lower than the outer diameter of tube 16. The catheter is then introduced into vessel 10 through an incision, not shown.

When the catheter has been properly emplaced relative to the atheroma 12, as shown in FIG. 1, the knob 36 is turned in the opposite direction to bring the sealing disc 38 into sealing relation with the end 40 of fitting 30. The resulting rotation of wire 18 and tip 20 results in full untwisting of bag 22. Valve 46 and plunger 44 are then operated to inflate the bag 22 with incompressible fluid. This causes both of the bags 22 and 24 to expand into pressing, compacting relation with atheroma 12, as shown in FIG. 4. After the atheroma has been compressed, the valve 46 is opened and the syringe 42 is operated to remove the fluid from the bag 22. As this occurs, the balloons 22 and 24 self-retract to the condition shown in FIG. 2. This occurs as a result of the elastic nature of the outer balloon element 24 and the fact that it is pre-conditioned to have a normal outer diameter in unstressed condition which is smaller than the outer diameter of tube 16. Additional lateral retraction of the balloon section of the catheter may then be obtained by axially twisting the bag by rotating the knob 36 to move it from the position of FIG. 4 to the position of FIG. 1. The twisting of the bag 22 and the consequent reduction of its diameter forces residual fluid out of the bag and causes it to drain out of the catheter through the now unsealed end 40 of fitting 30. The catheter may then be moved to a new section of atheroma to be treated or be withdrawn from the vessel, as the case may be.

The use of the subject catheter is particularly advantageous where the size of the artery or the size and nature of the occlusion calls for the use of a large diameter dilating bag. The self-retraction of the balloon section under the influence of the outer elastic balloon element together with the additional retraction which is provided by the twisting of the balloon element results in a catheter of smaller cross-sectional area than is presently available. This increases the number of situations in which this catheter can be used and allows for the treatment of sequential occlusions by repeated inflations and retractions. It also enables the catheter to get into occlusions which were previously inaccessible. Also, the outer balloon gives the balloon section of the catheter a relatively smooth profile, even though the inner balloon is fully twisted for maximum reduction of diameter, and this serves to minimize the possibility of embolisms resulting from catheter movement within blood vessles.

The inner balloon element 22 is preferably non-elastic, being formed, for example, of thin flexible vinyl tubing. The use of such non-elastic material for the inner balloon provides two advantages during catheter inflation. In the first place, non-elastic material has a higher yield strength than elastic material such as latex and the use of the non-elastic material therefor minimizes the possibility of balloon rupture and allows the use of higher dilatation pressures. Secondly, a non-elastic balloon will inflate to a given size determined by the size of its production mold whereas elastic balloons are subject to over-inflation with resulting damage to the vascular system and/or rupture at low dilatation pressures due to their relatively small yield strength.

The elastic balloon can be made in a mold, or it can be co-extruded over the catheter, or it can be made into a composite or laminate with the non-elastic vinyl material of balloon element 22.

It may be desirable, in order to minimize a longitudinal bunching-up of the balloon as a result of rotation of the wire 18, to provide a sliding connection between the wire 18 and knob 36, as by providing the wire 18 with a square cross-section and providing the knob with a square wire-receiving passageway. This would limit shortening of the balloon section of the catheter to that which results merely from the physical twisting of the balloon section.

What is claimed is:

1. A dilatation catheter comprising an elongated flexible tubular body member, a tip member in spaced relation to the distal end of said body member, an inner non-elastic bag secured to the tip member and the distal end of said body member, means to inflate and deflate said bag, an outer elastic bag secured to the tip member and the distal end of said body member operable to inflate in response to inflation of said inner bag and to deflate in response to deflation of said inner bag and to effect compaction of the deflated inner bag, and means operable from the proximal end of said body member when the catheter is in place within an artery to reduce the effective diameters of the bags when they are deflated comprising a wire extending longitudinally and fully through the body member and bags, said wire having its distal end secured to the tip member and having its proximal end secured to a rotatively manipulatable knob-like winding member, said wire being operable by selective rotation of said winding member to rotate the tip member relative to the body member and thereby axially twist and untwist the bags.

2. A dilatation catheter comprising an elongated flexible tubular body member, a tip member in spaced relation to the distal end of said body member, an inner non-elastic bag secured to the tip member and the distal end of said body member, means to inflate and deflate said bag, an outer elastic bag secured to the tip member and the distal end of said body member operable to inflate in response to inflation of said inner bag and to deflate in response to deflation of said inner bag and to effect compaction of the deflated inner bag, means operable from the proximal end of said body member when the catheter is in place within an artery to reduce the effective diameters of the bags when they are deflated comprising a wire extending through the body member and bags having its distal end secured to the tip member and having its proximal end secured to a winding member and operable by selective rotation of said winding member to rotate the tip member relative to the body member and thereby axially twist and untwist the bags, and an annular fitting attached to the proximal end of the body member, said winding member being in the form of a knob-like handle member threadably and sealingly connected to the proximal end of said fitting when said bags are untwisted and connected in backed-off relation to said fitting when said bags are twisted.

* * * * *